US006767889B1

(12) United States Patent
McCrae

(10) Patent No.: US 6,767,889 B1
(45) Date of Patent: Jul. 27, 2004

(54) INHIBITION OF ANGIOGENESIS BY HIGH MOLECULAR WEIGHT KININOGEN AND PEPTIDE ANALOGS THEREOF

(75) Inventor: Keith R. McCrae, Chagrin Falls, OH (US)

(73) Assignee: Temple University of the Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 09/437,912

(22) Filed: Nov. 9, 1999

Related U.S. Application Data

(60) Provisional application No. 60/107,833, filed on Nov. 10, 1998.

(51) Int. Cl.[7] ............................................. A01N 37/18
(52) U.S. Cl. ........................... 514/2; 514/12; 514/311; 514/16; 530/350; 530/300; 435/7.1; 435/6
(58) Field of Search .............................. 514/2, 12, 16, 514/311; 435/7.1, 6; 530/300, 350

(56) References Cited

U.S. PATENT DOCUMENTS

| | | | |
|---|---|---|---|
| 5,596,079 A | 1/1997 | Smith et al. | ................. 530/328 |
| 5,756,291 A | 5/1998 | Griffin et al. | ................... 435/6 |
| 5,786,365 A | 7/1998 | Heitsch et al. | ............... 514/311 |
| 5,817,748 A | 10/1998 | Miller et al. | .................... 530/30 |
| 5,830,671 A | 11/1998 | Dennis et al. | ............... 435/7.8 |
| 5,846,821 A | 12/1998 | Guerinot et al. | .......... 435/320.1 |
| 6,245,886 B1 * | 6/2001 | Halazonetis et al. | ......... 530/332 |
| 6,284,726 B1 * | 9/2001 | Colman et al. | ................. 514/2 |

FOREIGN PATENT DOCUMENTS

| | | | |
|---|---|---|---|
| JP | 0708217 A | * | 3/1995 |
| JP | 7082172 | | 3/1995 |
| JP | 8208692 | | 8/1996 |
| WO | WO 96/25434 | * | 8/1996 |
| WO | WO 96/41640 | | 12/1996 |
| WO | WO 97/05258 | * | 2/1997 |

OTHER PUBLICATIONS

Farh, Hoechst Japan, Accession No. AAR75188, 1995.*
Sumu, Sumitomo Seiyaku KK, Accession No. AAW07625, 1996.*
R.W. Colman, et al., Abstract #701, "Inhibition Of Angkiogenesis By Peptides Derived From Kininogen", *Blood* vol. 92, No. 10 Supplement 1, Nov. 15, 1998.
Heiko Herwald, et al., "Identification of an Endothelial Cell Binding Site on Kininogen Domain D3*", *The Journal of Biological Chemistry*, vol. 270, No. 24 pp. 14634–14641 (Jun. 16, 1995).
Satya P. Kunapuli et al., "Deletion Mutagenesis of High Molecular Weight Kininogen Light Chain", *The Journal of Biological Chemistry* vol. 268, No. 4, pp. 2486–2492 (Feb. 5, 1993).
Robert W. Colman et al., "Contact System: A Vascular Biology Modulator With Anticoagulant, Profibrinolytic, Antiadhesive, and Proinflammatory Attributes", *Blood,* vol. 90, No. 10 pp. 3819–3843 (Nov. 15, 1997).

Ahmed A.K. Hasan, et al., "Mapping the Cell Binding Site on High Molecular Weight Kininogen Domain 5*", *The Journal of Biological Chemistry,* vo. 270, No. 33 pp. 19256–19261 (Aug. 18, 1995).
Robert W. Colman, et al., "Binding of High Molecular Weight Kininogen to Human Endothelial Cells Is Mediated via a Site within domains 2 and 3 of the Urokinase Receptor", *J. Clin. Invest.,* vol. 100, No. 6, pp. 1481–1487 (Sep. 1997).
A.K. Hasan, et al., "The Carboxyl Terminus of Bradykinin and Amino Terminus of the Light Chain of Kininogens comprise an Endothelial Cell Binding Domain" Ahmed *The Journal of Biological Chemistry,* vo. 269, No. 50, pp. 31822–31830 (Dec. 16, 1994).
Mohammad M.H. Khan et al., "Three noncintiguous peptides comprise binding sites on high–molecular–weight kininogen to neutrophils", *The American Physiological Soceity (Heart Circ. Physiol.* 44): H145–150, vol. 275 (1998).
Yanina T. Wachtfogel et al., "High Molecular Weight Kininogen Binds to Mac-1 on Neutrophils by Its Heavy Chain (Domain 3) and its Light Chain (Domain 5)", *The Journal of Biological Chemistry,* vol. 269, No. 30, pp. 19307–19312 (Jul. 29, 1994).
Shinji Asakura et al., "Inhibition of Cell Adhesion by High Molecular Weight Kiniogen", *The Journal of Cell Biology,* vol. 116, No. 2, pp. 465–476 (Jan. 1992).
Lottspeich et al., "The Amino Acid Sequence of the Light Chain of Human High–Molecular–Mass Kininogen", *European Journal of Biochemistry,* 1985, vol. 152, pp. 307–314.
Takagaki et al., "Cloning and Sequence Analysis of cDNAs for Human High Molecular Weight and Low Molecular Weight Prekininogens", *The Journal of Biological Chemistry,* Jul. 15, 1985, vol. 260, No. 14, pp. 8601–8609.
Kitamura et al., "Structural Organization of Human Kininogen Gene and a Model for its Evolution", *The Journal of Biological Chemistry,* Jul. 15, 1985, vol. 260, No. 15, pp. 8610–8617.
Colman et al., Contact System: A Vascular Biology Modulator With Anticoagulant, Profibrinolytic, Antiadhesive, and proinflammatory Attributes. Blood, Nov. 15, 1997, vol. 90, No. 10, pp. 3819–3843.

* cited by examiner

Primary Examiner—Karen Cochrane Carlson
Assistant Examiner—Hope A. Robinson
(74) Attorney, Agent, or Firm—Drinker Riddle & Reath LLP

(57) ABSTRACT

Two-chain high molecular weight kininogen, and peptide analogs thereof having homology to sites within kininogen domain 5, are potent inhibitors of angiogenesis. The peptides have the formula $X_1$-His-Lys-X-Lys-$X_2$ wherein X is any amino acid, $X_1$ is from zero to twelve amino acids, more preferably from zero to six amino acids, most preferably from zero to three amino acids, and $X_2$ is from zero to twelve amino acids, more preferably from zero to six amino acids, most preferably from zero to three amino acids.

X is preferably an amino acid having a nonpolar side chain, or a polar side chain which is uncharged at pH 6.0 to 7.0. X is most preferably Asn, Phe or His. Methods of inhibiting endothelial cell proliferation and angiogenesis are provided.

29 Claims, 9 Drawing Sheets

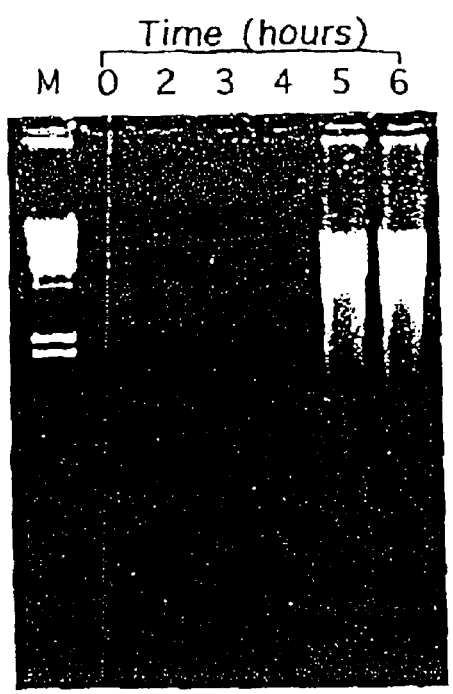
FIG. 7A
FIG. 7B

INHIBITION OF ANGIOGENESIS BY HIGH MOLECULAR WEIGHT KININOGEN AND PEPTIDE ANALOGS THEREOF

CROSS-REFERENCE TO RELATED APPLICATION

The benefit of U.S. provisional patent application No. 60/107,833 filed Nov. 10, 1998 is hereby claimed. The entire disclosure of application No. 60/107,833 is incorporated herein by reference.

FIELD OF THE INVENTION

The invention relates to therapeutic compounds and methods for inhibiting angiogenesis.

BACKGROUND OF THE INVENTION

Angiogenesis

Angiogenesis is the process in which new blood vessels grow into an area which lacks a sufficient blood supply. Angiogenesis commences with the erosion of the basement membrane surrounding endothelial cells and pericytes forming capillary blood vessels. Erosion of the basement membrane is triggered by enzymes released by endothelial cells and leukocytes. The endothelial cells then migrate through the eroded basement membrane when induced by angiogenic stimulants. The migrating cells form a "sprout" off the parent blood vessel. The migrating endothelial cells proliferate, and the sprouts merge to form capillary loops, thus forming a new blood vessel.

Angiogenesis can occur under certain normal conditions in mammals such as in wound healing, in fetal and embryonic development, and in the formation of the corpus luteum, endometrium and placenta. Angiogenesis also occurs in certain disease states such as in tumor formation and expansion, or in the retina of patients with certain ocular disorders. Angiogenesis can also occur in a rheumatoid joint, hastening joint destruction by allowing an influx of leukocytes with subsequent release of inflammatory mediators.

The evidence for the role of angiogenesis in tumor growth was extensively reviewed by O'Reilly and Folkman in U.S. Pat. No. 5,639,725, the entire disclosure of which is incorporated herein by reference. It is now generally accepted that the growth of tumors is critically dependent upon this process. Primary or metastatic tumor foci are unable to achieve a size of more than approximately 2 mm in the absence of neovascularization. Serial evaluation of transgenic mice predisposed to develop neoplasms has demonstrated that neovascularization of premalignant lesions precedes their evolution into tumors (Folkman et al., *Nature* 339:58–61, 1989), and that inhibition of angiogenesis delays the growth of such lesions, as well as their assumption of a malignant phenotype (Hanahan et al., *Cell* 86:353–364, 1996). In humans, several studies have demonstrated that increased density of microvessels within a tumor is associated with a poor clinical outcome (Weidner et al., *J Natl Cancer Inst* 84:1875–1887, 1992).

An emerging paradigm is that proteolytic fragments of plasma or extracellular matrix proteins regulate angiogenesis. To date, several polypeptides with such activities have been identified. These include angiostatin, which contains kringles 1–4 plasminogen (O'Reilly et al., *Cell* 79:315–328, 1994), endostatin, a 20 kD C-terminal fragment of collagen XVIII (O'Reilly et al., *Cell* 88:277–285, 1997), PEX, the hemopexin domain of matrix metalloprotease 2 (Brooks et al., *Cell* 92:391–400, 1998), the C-terminal 16 kD fragment of prolactin (Clapp et al., *Endocrinol* 133:1292–1299, 1993) and a 29 kD fragment of fibronectin (Homandberg et al., *Am J Pathol* 120:327–332; 1985). In addition, both intact thrombospondin 1 as well as peptides derived from its procollagen domain and properdin-like type-1 repeats express potent anti-angiogenic activity (Good et al., *Proc Nat Acad Sci USA* 87:6624–6628,1990); Tolsma et al., *J Cell Biol* 122:497–511, 1993. In preclinical models, several of these fragments inhibited tumor growth, and some induced tumor regression and dormancy (Boehm et al., *Nature* 390:404–407, 1997).

High Molecular Weight Kininogen

High molecular weight kininogen (HK) is a 120 kD glycoprotein containing heavy and light chains, comprised of domains 1 through 3, and 5 and 6, respectively (Kaplan et al., *Blood* 70:1–15, 1987). The heavy and light chains are linked by domain 4, which contains bradykinin, a nonapeptide which mediates several events including NO-dependent vasodilation (Weimer et al., *J Pharm Exp Therapeutics* 262:729–733, 1992). HK (also referred to as "single chain high molecular weight kininogen") binds with high affinity to endothelial cells, where it is cleaved to two-chain high molecular weight kininogen ($HK_a$) by plasma kallikrein. Bradykinin is released from HK through cleavage mediated by plasma kallikrein (Kaplan et al., *Blood* 70:1–15, 1987). This event occurs on the surface of endothelial cells following the activation of prekallikrein to kallikrein by an endothelial cell protease (Motta et al., *Blood* 91:515–528, 1998). Cleavage of HK to form $HK_a$ and release bradykinin occurs between Lys(362) and Arg(363). $HK_a$ contains a 62 kD heavy chain and a 56 kD light chain linked by a disulfide bond.

Conversion of HK to $HK_a$ is accompanied by a dramatic structural rearrangement, which has been demonstrated using rotary shadowing electron microscopy (Weisel et al. *J. Biol Chem* 269:10100–10106, 1994). $HK_a$, but not HK, has been shown to inhibit the adhesion of endothelial and other cell types to vitronectin (Asakura, *J. Cell Biol* 116:465–476, 1992).

Although the binding of HK to endothelial cells has been well characterized, comparatively little attention has been devoted to endothelial cell binding of $H_a$. Furthermore, although binding of bradykinin to endothelial cells induces well-defined responses, functional consequences of the direct binding of $HK_a$ have not been reported.

SUMMARY OF THE INVENTION

The compounds of the present invention are in the form of peptides which possess anti-angiogenic activity.

In all embodiments, the peptide may optionally comprise an amino-terminal and/or carboxy-terminal protecting group.

A compound of the formula $X_1$-His-Lys-X-Lys-$X_2$ (hereinafter "$X_1$-His-Lys-X-Lys-$X_2$ peptide") is provided wherein X is any amino acid, $X_1$ is from zero to twelve amino acids, more preferably from zero to six amino acids, most preferably from zero to three amino acids, and $X_2$ is from zero to twelve amino acids, more preferably from zero to six amino acids, most preferably from zero to three amino acids.

Preferably, X is an amino acid having a nonpolar side chain, i.e., Ala, Leu, Ile, Val, Pro, Phe, Trp, or Met; or X is an amino acid having a polar side group which is uncharged at pH 6.0 to 7.0, the zone of physiological pH, i.e., Ser, Thr, Tyr, Asn, Gln, Cys, or Gly. Most preferably, X is Asn, Phe or His.

Preferred compounds comprise fragments of HK. In one group of such preferred compounds, $X_1$ is
   (i) zero amino acids, or
   (ii) the segment His-Gly-His-Glu-Gln-Gln-His-Gly-Leu-Gly-His-Gly (SEQ ID NO:1) or N-terminal truncation fragment thereof containing at least one amino acid, and $X_2$ is
   (i) zero amino acids, or
   (ii) the segment Leu-Asp-Asp-Asp-Leu-Glu-His-Gln-Gly-Gly-His-Val (SEQ ID NO:2), or C-terminal truncation fragment thereof containing at least one amino acid.

In another group of such preferred compounds, $X_1$ is
   (i) zero amino acids, or
   (ii) the segment Gly-His-Lys-His-Lys-His-Gly-His-Gly-His-Gly-Lys (SEQ ID NO:3) or N-terminal truncation fragment thereof containing at least one amino acid, and $X_2$ is
   (i) zero amino acids, or
   (ii) the segment Gly-Lys-Lys-Asn-Gly-Lys-His-Asn-Gly-Trp-Lys-Thr (SEQ ID NO:4) or C-terminal truncation fragment thereof containing at least one amino acid.

According to a further preferred embodiment of the invention, the compound has a substantial amino acid homology to either the amino acid sequence His-Gly-His-Glu-Gln-Gln-His-Gly-Leu-Gly-His-Gly-His-Lys-Phe-Lys-Leu-Asp-Asp-Asp-Leu-Glu-His-Gln-Gly-Gly-His-Val (SEQ ID NO:5), or the amino acid sequence Gly-His-Lys-His-Lys-His-Gly-His-Gly-His-Gly-His-Lys-Asn-Lys-Gly-Lys-Lys-Asn-Gly-Lys-His-Asn-Gly-Trp-Lys-Thr (SEQ ID NO:6).

Exemplary and preferred compounds include:
(a) His-Gly-His-Glu-Gln-Gln-His-Gly-Leu-Gly-His-Gly-His-Lys-Phe-Lys-Leu-Asp-Asp-Asp-Leu-Glu-His-Gln-Gly-Gly-His-Val (SEQ ID NO:5);
(b) Gly-His-Lys-Phe-Lys-Leu-Asp-Asp-Asp-Leu-Glu-His-Gln-Gly-Gly-His (SEQ ID NO:7);
(c) Gly-His-Lys-His-Lys-His-Gly-His-Gly-His-Gly-Lys-His-Lys-Asn-Lys-Gly-Lys-Lys-Asn-Gly-Lys-His-Asn-Gly-Trp-Lys-Thr (SEQ ID NO:6);
(d) Lys-His-Gly-His-Gly-His-Gly-Lys-His-Lys-Asn-Lys-Gly-Lys-Lys-Asn (SEQ ID NO:8); and
(e) His-Lys-Asn-Lys-Gly-Lys-Lys-Asn-Gly-Lys-His-Asn-Gly-Trp-Lys-Thr (SEQ ID NO:9).

The invention also encompasses a method of inhibiting endothelial cell proliferation comprising contacting endothelial cells with HK, $HK_a$ or a $X_1$-His-Lys-X-Lys-$X_2$ peptide.

The invention also encompasses a method of inducing apoptosis of endothelial cells comprising contacting endothelial cells with HK, $HK_a$ or a $X_1$-His-Lys-X-Lys-$X_2$ peptide.

The invention is also a composition comprising a pharmaceutically effective carrier and HK, $HK_a$ or a $X_1$-His-Lys-X-Lys-$X_2$ peptide.

The invention is also a method of inhibiting angiogenesis in a mammal in need of such treatment comprising administering to said mammal a therapeutically effective amount of a composition comprising a pharmaceutically effective carrier and HK, $HK_a$ or a $X_1$-His-Lys-X-Lys-$X_2$ peptide. The mammal treated is preferably a human being.

Other aspects and advantages of the present invention are described in the drawings and in the following detailed description of the preferred embodiments thereof.

Abbreviations and Short Forms

The following abbreviations and short forms are used in this specification.

"BFGF" is recombinant human basic fibroblast growth factor.

"HK" means the mature form of high molecular weight kininogen, and any allelic variations thereof. By "mature" is meant the post-translationally-modified form of HK which results from cleavage of an eighteen amino acid leader from the initially translated molecule. All numbering with respect to amino acid positions of HK is from the N-terminus of the mature form as position 1. "HK" is synonymous with "single chain HK", the mature form of high molecular weight kininogen prior to cleavage by kallikrein and the formation of two chain high molecular weight kininogen.

"$HK_a$" means two-chain high molecular weight kininogen, the product of kallikrein cleavage of mature high molecular weight kininogen, and any allelic variations thereof.

"HDMVEC" means human dermal microvascular endothelial cells.

"HGF" means hepatocyte growth factor.

"HUVEC" means human umbilical vein endothelial cell

"PDGF" is platelet-derived growth factor.

"TGF-β" is transforming growth factor-β.

"VEGF" means vascular endothelial cell growth factor.

"$X_1$-His-Lys-X-Lys-$X_2$ peptide" means a compound of the indicated formula wherein X, $X_1$ and $X_2$ are defined as above.

Amino Acid Abbreviations

The nomenclature used to describe polypeptide compounds of the present invention follows the conventional practice wherein the amino group is presented to the lest and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified. In the amino acid structure formulae, each residue is generally represented by a one-letter or three-letter designation, corresponding to the trivial name of the amino acid, in accordance with the following schedule:

| A | Alanine | Ala |
|---|---|---|
| C | Cysteine | Cys |
| D | Aspartic Acid | Asp |
| E | Glutamic Acid | Glu |
| F | Phenylalanine | Phe |
| G | Glycine | Gly |
| H | Histidine | His |
| I | Isoleucine | Ile |
| K | Lysine | Lys |
| L | Leucine | Leu |
| M | Methionine | Met |
| N | Asparagine | Asn |
| P | Proline | Pro |
| Q | Glutamine | Gln |
| R | Arginine | Arg |
| S | Serine | Ser |
| T | Threonine | Thr |
| V | Valine | Val |
| W | Tryptophan | Trp |
| Y | Tyrosine | Tyr |

Definitions

The following definitions, of terms used throughout the specification, are intended as an aid to understanding the scope and practice of the present invention.

"Angiogenesis" means the generation of new blood vessels into a tissue or organ.

"Apoptosis" means a process of programmed cell death.

A "peptide" is a compound comprised of amino acid residues covalently linked by peptide bonds.

The expression "amino acid" as used herein is meant to include both natural and synthetic amino acids, and both D and L amino acids. "Natural amino acid" means any of the twenty primary, naturally occurring amino acids which typically form peptides, polypeptides, and proteins. "Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention, as long as anti-angiogenic activity is maintained.

Amino acids have the following general structure:

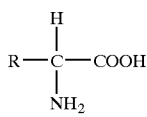

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. Peptides comprising a large number of amino acids are sometimes called "polypeptides". The amino acids of the peptides described herein and in the appended claims are understood to be either D or L amino acids with L amino acids being preferred.

"Homology" means similarity of sequence reflecting a common evolutionary origin. Peptides or proteins are said to have homology, or similarity, if a substantial number of their amino acids are either (1) identical, or (2) have a chemically similar R side chain. Nucleic acids are said to have homology if a substantial number of their nucleotides are identical.

As used herein, "protected" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3–88 (Academic Press, New York, 1981) for suitable protecting groups.

As used herein, "protected" with respect to a terminal carboxyl group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

"Substantial amino acid sequence homology" means an amino acid sequence homology greater than about 30%, preferably greater than about 60%, more preferably greater than about 80%, and most preferably greater than about 90%.

By "N-terminal truncation fragment" with respect to an amino acid sequence is meant a fragment obtained from a parent sequence by removing one or more amino acids from the N-terminus thereof.

By "C-terminal truncation fragment" with respect to an amino acid sequence is meant a fragment obtained from a parent sequence by removing one or more amino acids from the C-terminus thereof.

DESCRIPTION OF THE FIGURES

FIGS. 7A and 7B show DNA fragmentation in endothelial cells exposed to $HK_a$ as a function of time (at 30 nM concentration) and concentration (at 12 hours), respectively.

DETAILED DESCRIPTION OF THE INVENTION

Figure 1:
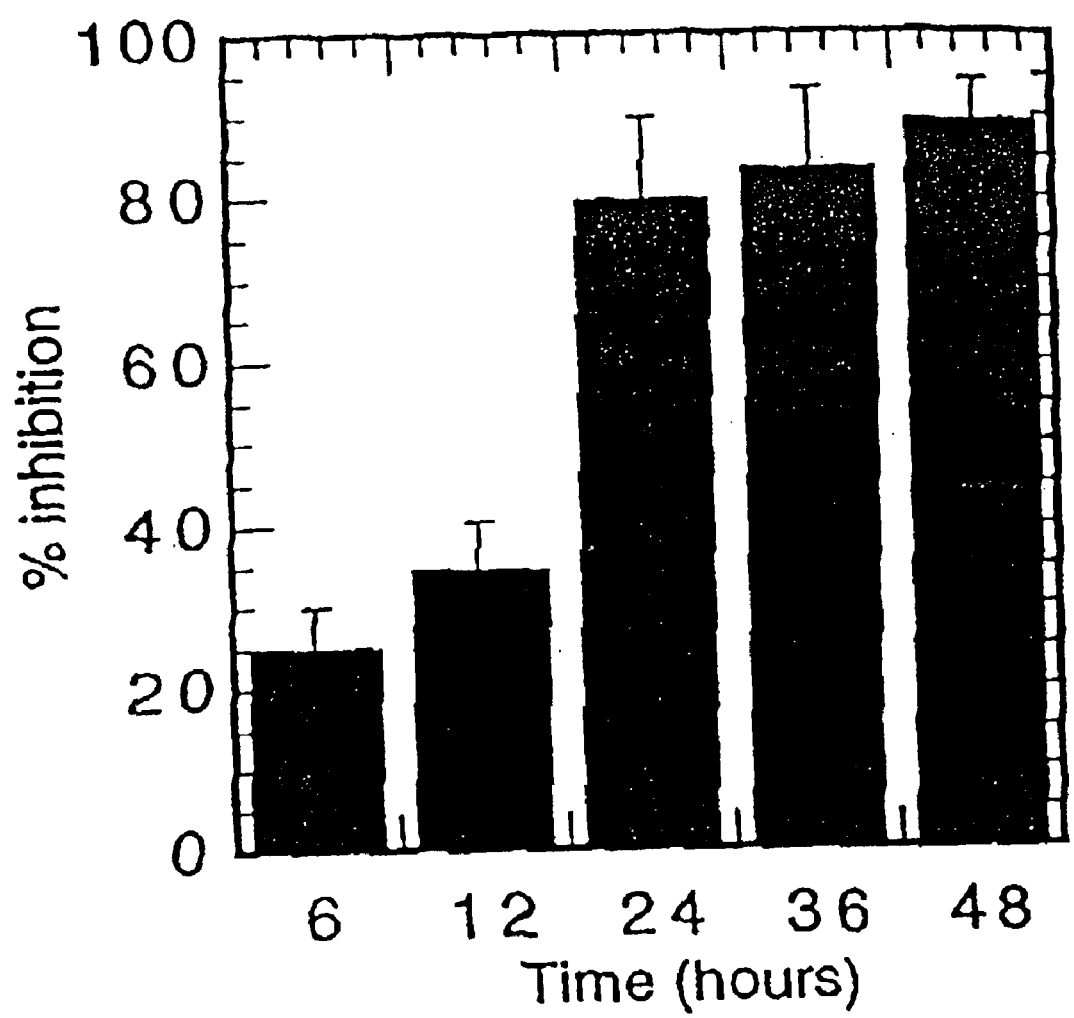
FIG. 1 shows the inhibition of endothelial cell proliferation over time following contact with $HK_a$.

The present invention is based upon the discovery that $HK_a$ and peptide analogs of certain sites in the HK domain 5 inhibit endothelial cell proliferation and/or induce endothelial cell apoptosis. These activities confer upon $HK_a$ and the $X_1$-His-Lys-X-Lys-$X_2$ peptides the ability to inhibit cytokine-driven angiogenesis in vivo.

Antiproliferative effects are observed at concentrations below 1.0 nM. The use among different laboratories of endothelial cells of different origin, and/or varying concentrations of endothelial cell growth factors, makes a direct comparison of the relative potency of $HK_a$ and previously-reported anti-angiogenic polypeptides difficult. However, the observations made herein suggest that the in vitro potency of $HK_a$ in this regard is similar to that of angiostatin (O'Reilly et al., Cell 79:315–328, 1994), endostatin (O'Reilly et al., Cell 88:277–285, 1997) and TSP-1 (Good et al., Proc Nat Acad Sci USA 87:6624–6628, 1990). Furthermore, when the plasma concentration (670 nM) of the parent molecule, HK, is considered, it is apparent that the anti-angiogenic activity of $HK_a$ and the $X_1$-His-Lys-X-Lys-$X_2$ peptides is physiologically significant.

The effects of $HK_a$, and thus the effects of the $X_1$-His-Lys-X-Lys-$X_2$ peptides also, are cell specific. No inhibition of the proliferation of either human aortic smooth muscle cells or HEK 293 cells by $HK_a$ is observed. According to the assays utilized herein, $HK_a$, potently inhibits the proliferation of human umbilical vein and microvascular endothelial cells in vitro in response to various pro-angiogenic growth factors: bFGF, VEGF, hepatocyte growth factor, TGF-β and PDGF. Inhibition of endothelial cell proliferation is detected within 6 hours of exposure of the cells to $HK_a$, and is accompanied by morphologic and biochemical evidence of cell apoptosis.

Furthermore, as shown herein, $HK_a$ is effective in an in vivo model of angiogenesis. $HK_a$ inhibits the ingrowth of new blood vessels into a reconstituted extracellular matrix (MATRIGEL® Becton, Dickinson and Co., Bedford, Mass.) containing the pro-angiogenic growth factor bFGF implanted subcutaneously into mice.

Without wishing to be bound by any theory, the observation that $HK_a$, but not single chain HK, inhibits endothelial cell proliferation suggests that the structural change which the molecule undergoes following kallikrein-mediated cleavage is important for expression of its anti-angiogenic activity.

The mature human HK amino acid sequence is set forth in the recent review by Colman and Schmaier, Blood, 90:3819–3843 (1997), for example. $HK_a$ generated by plasma kallikrein cleavage of HK differs from HK in that it lacks the nine amino acid segment comprising HK amino acids 363–371. This segment is released from HK as the nonapeptide bradykinin. The two chains of HK resulting from the elimination of bradykinin remain linked by a disulfide bond between cysteine residues at positions 10 and 656 of mature HK. The N-terminal and C-terminal chains of $HK_a$ generated by plasma kallikrein cleavage of HK and release of bradykinin are known as HK "heavy" and "light" chains, respectively. $HK_a$ may be generated by treating HK with plasma kallikrein, according to well-known methods. $HK_a$ is also commercially available. Furthermore, other enzymes, such as plasmin, chymotrypsin or matrix metalloproteases, for example, may degrade HK to release peptides similar to those described herein.

HK domain 5 spans HK residues 384–502. Located within domain 5 are two separate segments characterized by the sequence His-Lys-X-Lys. The first such segment occurs at position 457–460. The second segment occurs at position 488–491. $HK_a$-derived peptides containing the His-Lys-X-Lys sequence inhibit endothelial cell proliferation and are useful as anti-angiogenic agents.

The $X_1$-His-Lys-X-Lys-$X_2$ peptides of the present invention may be recombinant peptides, natural peptides, or synthetic peptides. They may also be chemically synthesized, using, for example, solid phase synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures. See Merrifield, J. Amer. Chem. Soc. 85:2149–54 (1963) and Science 50:178–85 (1965). Additional information about the-solid phase synthesis procedure can be had by reference to the treatise by Steward and Young (Solid Phase Peptide Synthesis, W. H. Freeman & Co., San Francisco, 1969, and the review chapter by Merrifield in Advances in Enzymology 32:221–296, F. F. Nold, Ed., Interscience Publishers, New York, 1969; and Erickson and Merrifield, The Proteins 2:255 et seq. (ed. Neurath and Hill), Academic Press, New York, 1976. The synthesis of peptides by solution methods is described in Neurath et al., eds. (The Proteins, Vol. 11, 3d Ed., Academic Press, NY (1976)).

Crude peptides may be purified using preparative high performance liquid chromatography. The amino terminus may be blocked according, for example, to the methods described by Yang et al. (FEBS Left. 272:61–64 (1990)).

Peptide synthesis includes both manual and automated techniques employing commercially available peptide synthesizers. The $X_1$-His-Lys-X-Lys-$X_2$ peptides may be prepared by chemical synthesis and biological activity can be tested using the methods disclosed herein.

Alternatively, the $X_1$-His-Lys-X-Lys-$X_2$ peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in Maniatis (Molecular Cloning, Cold Spring Harbor Laboratories, 1982), and in Sambrook (Molecular Cloning, Cold Spring Harbor Laboratories, Second Ed., 1989), and in Ausubel (Current Protocols in Molecular Biology, Wiley and Sons, 1987), which are incorporated by reference. The complete cDNA of human HK is reported, for example, by Takagi et al., J. Biol. Chem. 260:8601–8609 (1985), the entire disclosure of which is incorporated herein by reference. From this nucleic acid sequence, synthetic genes encoding $HK_a$-derived peptides may be synthesized directly on a DNA synthesizer, or may be synthesized as complementary oligonucleotides which are ligated together to form the synthetic gene.

The nucleic acids encoding $HK_a$-derived peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate to be immunized. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lacI, lacZ, T3, T7, lambda Pr' PI' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VIII), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV-40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include but are not limited to SV40 polyadenylation signals and LTR polyadenylation signals.

The $X_1$-His-Lys-X-Lys-$X_2$ peptides prepared by either chemical synthesis or recombinant DNA technology may then be assayed for biological activity according to the assay methods described herein.

In some embodiments, the peptides of the present invention may be used in the form of a pharmaceutically acceptable salt.

Suitable acids which are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The present invention provides methods for inhibiting angiogenesis. A preferred embodiment is a method of inhibiting the proliferation of endothelial cells, or obtaining apoptosis of such cells. Accordingly, HK, $HK_a$ and/or one or more $X_1$-His-Lys-X-Lys-$X_2$ peptides is administered to a patient in need of such treatment. A therapeutically effective amount of the drug may be administered as a composition in combination with a pharmaceutically carrier. Although HK is considerably less anti-angiogenic than $HK_a$, it is possible that upon administration HK will be converted to $HK_a$, and may therefore serve as a prodrug for $HK_a$. In particular, it is believed that HK may be rapidly converted to $HK_a$ in tumors, or further cleaved by tumor-derived enzymes to release peptides the same or similar to the peptides disclosed herein.

The ability of $HK_a$ to inhibit the proliferation of endothelial cells cultured on different extracellular matrix (ECM) proteins was determined. $HK_a$ (1 nM) potently inhibited the proliferation of HUVEC cultured on gelatin, laminin and MATRIGEL® (Becton, Dickinson and Co.), though slightly less potent inhibition, largely overcome by high concentrations of $HK_a$ (50 nM), occurred when cell were cultured on fibronectin or vitronectin. Intermediate effects were observed when cells were cultured on fibrinogen, though cells cultured on collagen types I or IV were resistant to the antiproliferative activity of $HK_a$. In keeping with the results of proliferation assays, $HK_a$ caused apoptosis of endothelial cells cultured on gelatin, but not on collagen, and of cells cultured at low density, but not under confluent or near confluent conditions. Without wishing to be bound by any theory, it appears that mature endothelial cells residing on an intact, collagen-rich basement membrane may be protected from $HK_a$-induced apoptosis, and that $HK_a$ might selectively target angiogenic endothelial cells in a protease-rich tumor milleu in which ECM is partially degraded.

Pharmaceutically acceptable carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

The compositions may be administered by any convenient route which will result in delivery to the site of undesired angiogenesis in an amount effective for inhibiting that angiogenesis from proceeding. Modes of administration include, for example, orally, rectally, parenterally (intravenously, intramuscularly, intraarterially, or subcutaneously), intracistemally, intravaginally, intraperitoneally, locally (powders, ointments or drops), or as a buccal or nasal spray or aerosol. The compositions can also be delivered through a catheter for local delivery at a target site, or via a biodegradable polymer. The compositions may also be complexed to ligands, or antibodies, for targeted delivery of the compositions.

The compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small (e.g., less than about 8–10 amino acids) other preferred routes of administration are intranasal, sublingual, and the like. Intravenous or subcutaneous administration may comprise, for example, injection or infusion.

The compositions according to the invention can be administered in any circumstance in which inhibition of angiogenesis is desired. Disease states which may be treated include but are not limited to cancer, rheumatoid arthritis, and certain ocular disorders characterized by undesired vascularization of the retina. Because the peptides of the invention are anti-angiogenic, cancers characterized by the growth of solid tumors through angiogenesis of the tissue surrounding the tumor site may be treated according to the invention.

The amount of active agent administered depends upon the degree of the anti-angiogenic effect desired. Those skilled in the art will derive appropriate dosages and schedules of administration to suit the specific circumstances and needs of the patient. Typically, dosages are from about 0.1 to about 100, preferably from about 0.5 to about 50, most preferably from about 1 to about 20, mg/kg of body weight. The active agent may be administered by injection daily, over a course of therapy lasting two to three weeks, for example. Alternatively, the agent may be administered by continuous infusion, such as via an implanted subcutaneous pump.

Peptides which inhibit endothelial cell proliferation by at least 30%, more preferably by at least 50%, most preferably by at least 70%, when incubated with such cells at a concentration of 5 $\mu$M are preferred. For purposes of this preference, percent inhibition of proliferation is determined according to the procedure and formula set forth in Example 1, part A, below.

EXAMPLES

The present invention is illustrated by the following non-limiting examples.

Materials

The materials utilized in the Examples were sourced as follows. Tissue culture medium and reagents were obtained from Mediatech (Herndon, Va.). Fetal bovine serum was from Hyclone (Logan, Utah). Endothelial growth supplement was purified from bovine hypothalamii, as previously described (Maciag et al., *Proc natl Acad Sci* 76:5674–5678, 1979). Recombinant human basic fibroblast growth factor (bFGF), vascular endothelial cell growth factor (VEGF) and hepatocyte growth factor (HGF) were obtained from Collaborative Biomedical Products/Becton Dickinson (Bedford, Mass.). Platelet-derived growth factor (PDGF) and transforming growth factor β (TGF-β) were from R&D Systems (Minneapolis, Minn.). Gelatin was purchased from Sigma (St. Louis, Mo.). Single and two-chain high molecular weight kininogen were obtained from Enzyme Research Labs (South Bend, Ind.). $HK_a$ was >98% two-chain, as determined using 10% SDS-PAGE after reduction. Low molecular weight kininogen was purchased from American Research Products, (Belmont, Mass.). Bradykinin was from Peninsula Laboratories (Belmont, Calif.), and rabbit anti-bradykinin antiserum from Sigma. All $HK_a$ preparations used in these studies contained less than <0.01 EU/ml of endotoxin, as determined using the E-Toxate (Limulus Amoebocyte) assay (Sigma).

Synthetic Peptides

Synthetic peptides were synthesized on a Rainin Symphony multiple peptide synthesizer, using Fmoc chemistry. All resins (AnaSpec) used for solid phase synthesis were Wang resins preloaded with the first amino acid. Fmoc amino acids were purchased from Perseptive Biosystems, with side chain protective groups as follows: trityl (Asn, Cys, Gln, and His), Boc (Lys and Trp), Ombu (Asp and Glu), T.U. (Ser, Thr and Tyr) and P.G. (Arg). Deprotection of the Fmoc group was performed in piperidine in dimethtylformamide (DMF). Coupling was carried out done in HBTU in N-methylmorpholine/DMF as the activator. Standard synthesis cycles were 3×30" washes with DMF, 3×15" deprotection with piperidine, 6×20" DMF washes, 45 minute coupling with amino acid and activator followed by 3×30" DMF washes.

Peptides were cleaved off the solid phase support with cleavage cocktail consisting of 88:5:5:2 (TFA:water:phenol:triisopropylsilane). Cleavage was done on the synthesizer. Peptides were precipitated with ether, pelleted by centrifugation, washed three times with ether and then allowed to dry. HPLC was carried out on a Beckman HPLC system using Rainin Dynamax Reversed Phase columns and an acetonitrile gradient in water. The desired peptide was detected during elution by off line MALDI-TOF mass spectrophotometry using a Perseptive Biosystems Voyager instrument. Purified peptides were lyophilized and then reanalyzed by MALDI-TOF mass spectrophotometry.

Cell Culture Methods

The basic cell culture methods of the Examples are described as follows. Human umbilical vein endothelial cells (HUVEC) and human aortic smooth muscle cells were isolated and cultured as previously described (Graham et al, *Blood* 91:3300–7 1998). Human dermal microvascular endothelial cells (HDMVEC) were obtained from Clonetics (San Diego, Calif.) and cultured under identical conditions. All cells in these studies were of passage 3 or lower.

Example 1

Effect of Single-Chain and Two-Chain High Molecular Weight Kininogen on Endothelial Cell Proliferation A. Experimental To assess the effect of $HK_a$ on endothelial cell proliferation, cells were suspended at a concentration of 30,000 cells/ml in Medium 199 (M199) containing 2% FCS. One hundred microliters of this suspension was then plated in individual wells of a 96 well microplate precoated with 1% gelatin. After incubation for 2 hours, at 37° C., to allow cells to adhere and spread, medium was removed and replaced with fresh M199 containing (i) 2% FCS, (ii) 10 $\mu$M $ZnCl_2$, (iii) 10 ng/ml bFGF, VEGF, HGF, TGF-β or PDGF and (iv) 50 $\mu$M HK or $HK_a$. Cells were then incubated for 48 hours at 37° C., at which time the relative numbers of cells in each well were determined using the Cell Titer® $Aq_{ueous}$ cell proliferation assay (Promega, Madison, Wis.). Briefly, 20 $\mu$l of a 19:1 (V:N) mixture of (3(4,5-dimethylthiazol-2-yl)-5-(3-carboxymethylphenyl)-2-(4-sulfophenyl)-2H-tetrazolium (MTS) and phenazine methosulfate (PMS) was added to each well, and after an additional hour of incubation, $A_{490}$ was measured using a BioRad model EL311 microplate reader. The percent inhibition of cell proliferation by $HK_a$ was determined using the formula:

$$\% \text{ inhibition} = (1 - [(A_{490(+GF, HKa)} - A_{490 (-GF)})/(A_{490(+GF)} - A_{490(-GF)})]) \times 100,$$

where (+GF) and (−GF) represent proliferation in the presence or absence of added growth factor, and (+GF, $HK_a$)

represents proliferation in the presence of both growth factor and $HK_a$. The significance of differences in relative endothelial cell proliferation cell numbers at the end of the proliferation assays was determined using the Student's two-tailed T-test for paired samples.

B. Results

Figure 2:
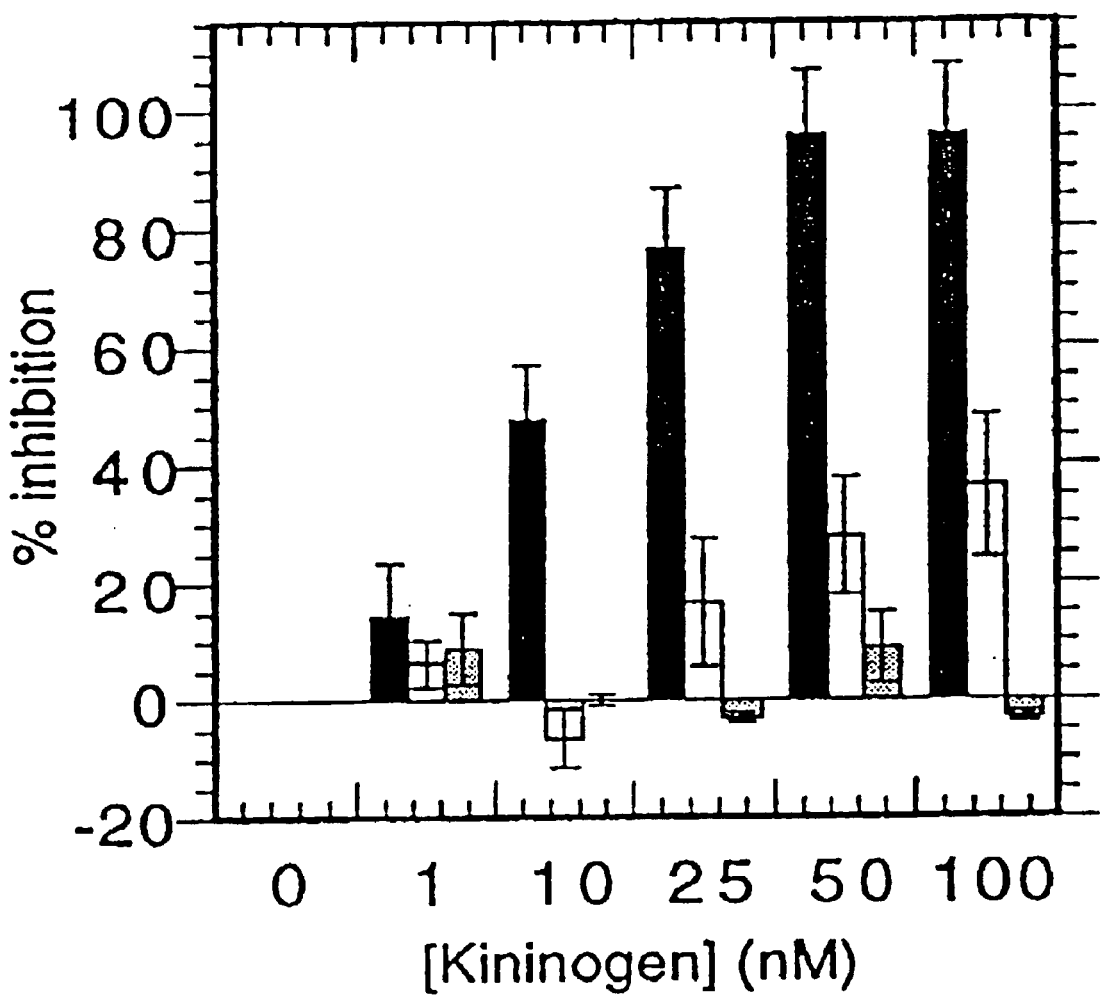
FIG. 2 shows the concentration-dependent inhibition of endothelial cell proliferation by $HK_a$ (fine crosshatched bars), HK (white bars) and low molecular weight kininogen (course crosshatched bars). Low molecular weight kininogen is non-inhibitory.

Inhibition of endothelial cell proliferation by $HK_a$ was apparent within 6 hours after its addition to cells, at which time cell spreading appeared to be diminished, and the cells began to display a more rounded morphology. However, the extent to which proliferation was inhibited increased progressively with longer exposure of cells to $HK_a$ (FIG. 1). Inhibition of endothelial cell proliferation by $HK_a$ occurred in a concentration-dependent manner; modest inhibition (14%) of bFGF (10 ng/ml)—stimulated proliferation occurred at an $HK_a$ concentration of <1.0 nM, while $HK_a$ inhibited proliferation by 50% at a concentration of approximately 8 nM (FIG. 2).

Single-chain HK, low molecular weight kininogen and bradykinin were tested in the same manner. $HK_a$ inhibited endothelial cell proliferation to a much greater extent than single-chain HK. Low molecular weight kininogen, which is derived from alterative splicing of the kininogen gene and contains the entire HK light chain, domain 4 and a truncated domain 5 containing only 12 amino acids, had no effect on endothelial cell proliferation (FIG. 2). Finally, bradykinin did not inhibit proliferation, and anti-bradykinin antibodies did not inhibit the anti-proliferative effect of $HK_a$ (not shown). The latter results exclude the possibility that contamination of $HK_a$ with trace amounts of bradykinin was responsible for its ability to inhibit endothelial cell proliferation. Single-chain HK modestly inhibited endothelial cell proliferation.

These results demonstrate that $HK_a$ is a potent and rapid inhibitor of endothelial cell proliferation in vitro, and that these activities occur within a concentration range similar to that of previously-described anti-angiogenic polypeptides.

Figure 3:
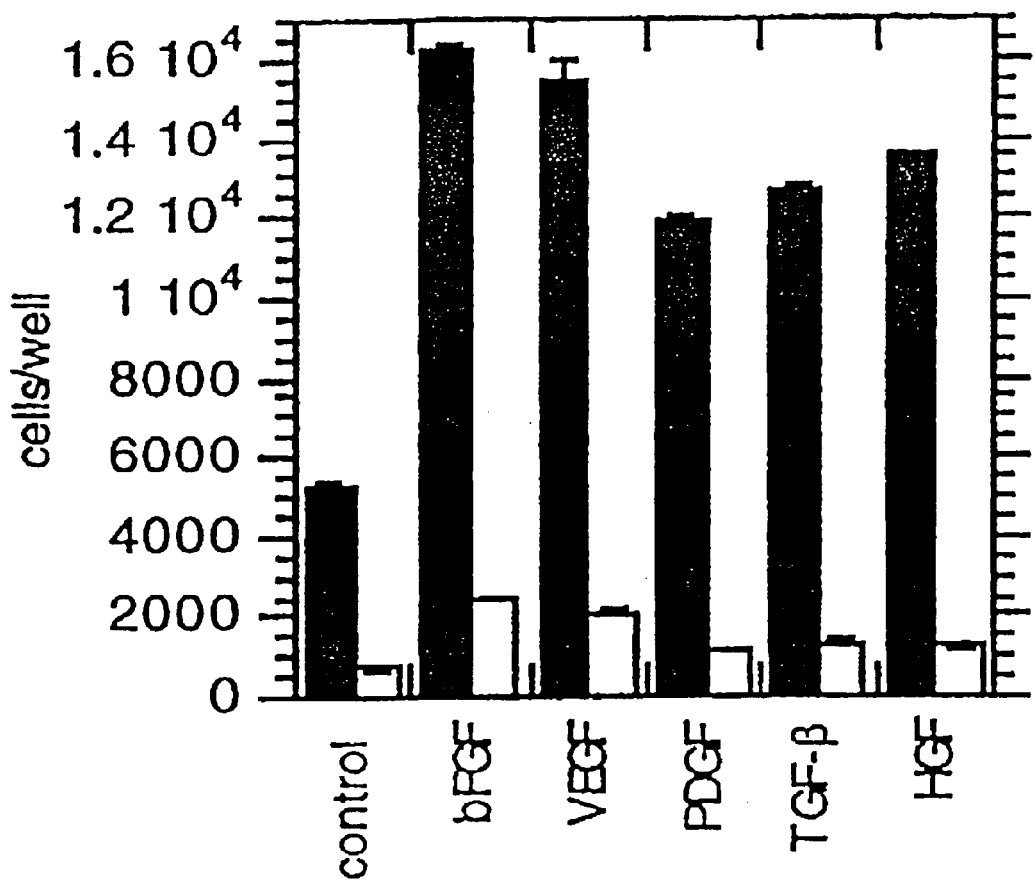
FIG. 3 shows the ability of 30 nM $HK_a$ to inhibit endothelial cell proliferation stimulated by a variety of growth factors.

$HK_a$ inhibited the proliferation of human endothelial cells in response to a number of mitogens, including bFGF, VEGF, HGF, TGF-β and PDGF, equally well (FIG. 3). The mitogenic activity of each of these factors is mediated through interactions with distinct receptors. Thus, without wishing to be bound by any theory, these results imply that the mechanism(s) by which $HK_a$ and the $HK_a$ peptides inhibits endothelial cell proliferation is unlikely to depend upon inhibition of growth factor binding.

Figure 4:
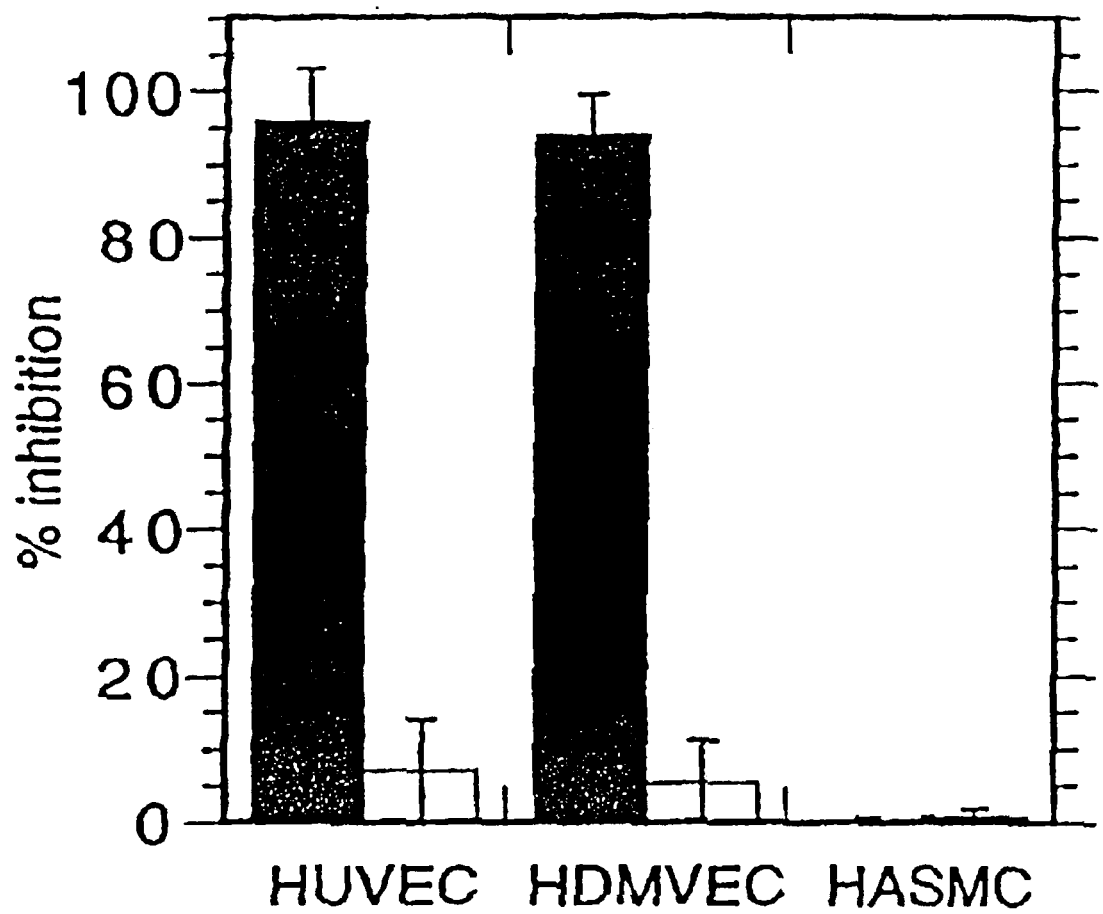
FIG. 4 shows that $HK_a$ inhibits proliferation of two types of endothelial cells (HUVEC and HDMVEC), but not human aortic smooth muscle cells (HASMC).
Figure 5:
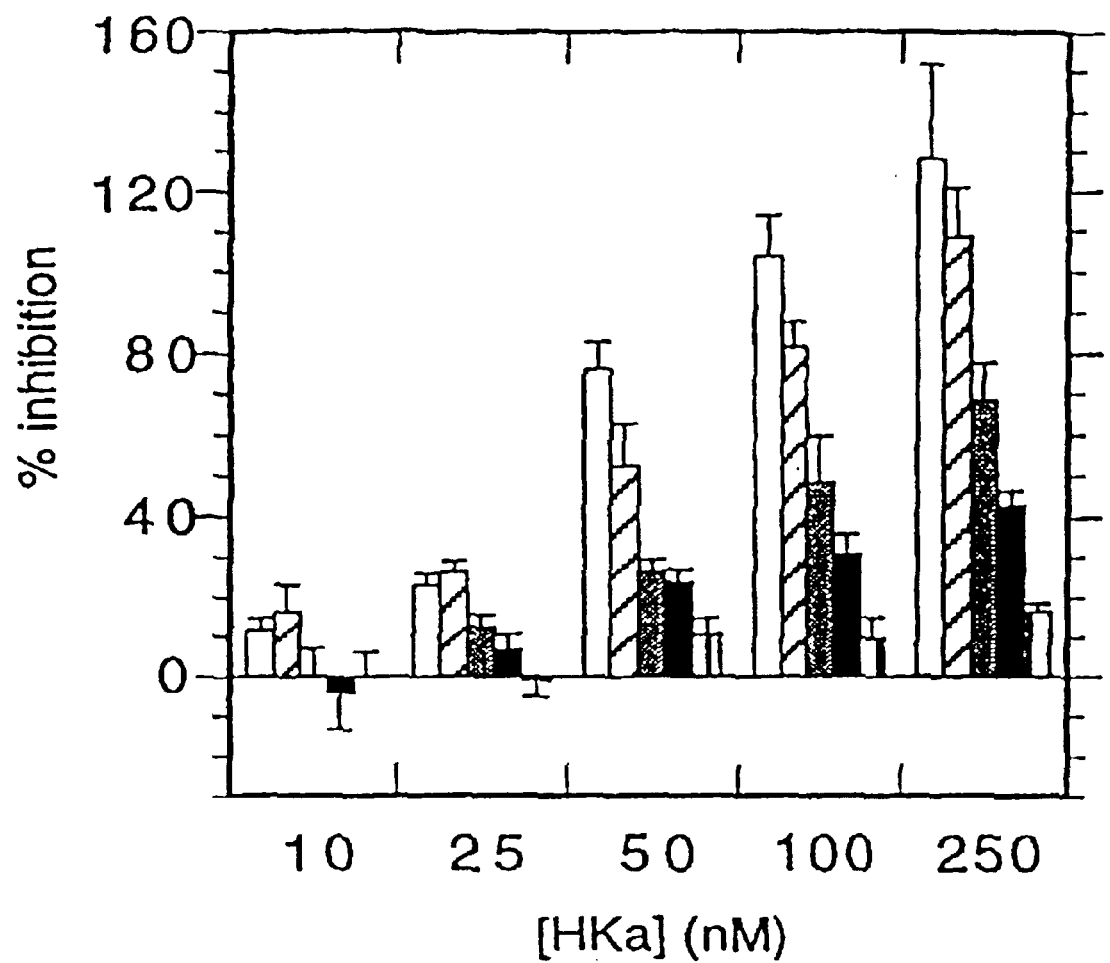
FIG. 5 shows the inhibition of endothelial cell proliferation as a function of HKa concentration and cell density in the culture. White bars=1,500 cells/well; course crosshatched bars=3,000 cells/well; fine crosshatched bars=6,000 cells/well; very fine crosshatched bars=12,000 cells/well; vertically hatched bars=24,000 cells/well.

$HK_a$ inhibited the proliferation of HUVEC and HDM-VEC with similar potency but did not affect the proliferation of human aortic smooth muscle cells (FIG. 4) or HEK 293 cells (not shown), demonstrating that $HK_a$'s antiproliferative effects were endothelial cell-specific. Furthermore, the ability of $HK_a$ to inhibit endothelial cell proliferation was inversely proportional to the density of the cell culture (FIG. 5), suggesting that its effects may be at least partially dependent upon the rate of cell proliferation and DNA synthesis.

In other experiments, the ability of $HK_a$ to inhibit the proliferation of endothelial cells cultured on different extracellular matrix (ECM) proteins. $HK_a$ (1 nM) potently inhibited the proliferation of HUVEC cultured on gelatin, laminin and MATRIGEL® (Becton, Dickinson and Co.), though slightly less potent inhibition, largely overcome by high concentrations of $HK_a$ (50 nM), occurred when cells were cultured on fibronectin or vitronectin. Intermediate effects were observed when cells were cultured on fibrinogen, though cells cultured on collagen types I or IV were resistant to the antiproliferative activity of $HK_a$.

Example 2

Apoptosis of Endothelial Cells Induced by Two-Chain High Molecular Weight Kininogen A. Experimental Induction of endothelial cell apoptosis after exposure of cells to $HK_a$ was determined using three assays.

Cells plated on glass coverslips were cultured in the absence or presence of 30 nM $HK_a$ for periods of 2–24 hours. Cells were then fixed for 1 hour in phosphate-buffered saline (PBS) containing 1% formaldehyde, and stained for 2 hours with a solution containing 1 μg/ml of 4',6'-diamidino-2-phenylindole dihydrochloride (DAPI) and 10 μg/ml of sulforhodamine 101 (Molecular Probes, Eugene Oreg.). Stained cells were visualized by UV illumination using a Nikon Microphot FXA microscope (objective 40X, Neofluor). Nuclear condensation, fragmentation and hyperchromaticity were considered to reflect apoptosis.

DNA fragmentation after exposure of cells to $HK_a$ was also directly assessed. Briefly, cells were cultured in the absence or presence of 30 nM $HK_a$, for varying periods, and DNA isolated following cell lysis in a buffer containing 20 mm Tris-HC1, pH 7.4, 5 mM ethylenediamine tetraacetic acid (EDTA) and 0.4% Triton X-100. After centrifugation to remove nuclei and insoluble material, the supernatant was extracted with an equal volume of phenol:chloroform:1-isopropanol (25:24:1), and DNA precipitated by the addition of 50 μl of 4 M LiCl and 500 pi 2-propanol. Precipitated DNA was dried using a Speed-Vac (Savant, Holbrook, N.Y.), resuspended in 20 mM Tris-HC1, pH 7.4, containing 5 mM EDTA and incubated for 30 minutes in the presence of 0.1 mg/ml RNase A. Samples were then analyzed by 0.8% agarose gel electrophoresis and visualized under UV light after staining with ethidium bromide.

Apoptosis was also confirmed by using the TUNEL reaction (In Situ Cell Death Detection Kit, Boehringer Mannheim, Indianapolis, Ind.) to label control cells and those exposed to $HK_a$ with fluorescein-conjugated dUTP, per the manufacturer's protocol. Labeled cells were then analyzed by flow cytometry.

B. Results

Figure 6A:
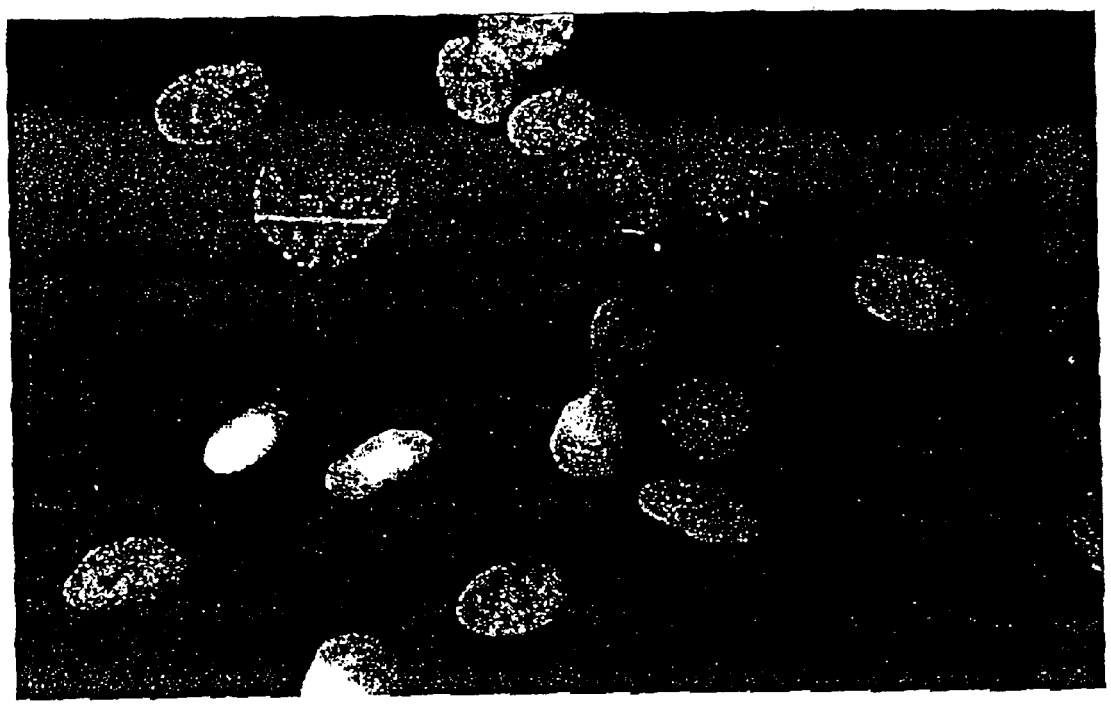
FIG. 6A shows endothelial cells after staining with 4',6'-diamidino-2-phenylindole hydrochloride.
Figure 6B:
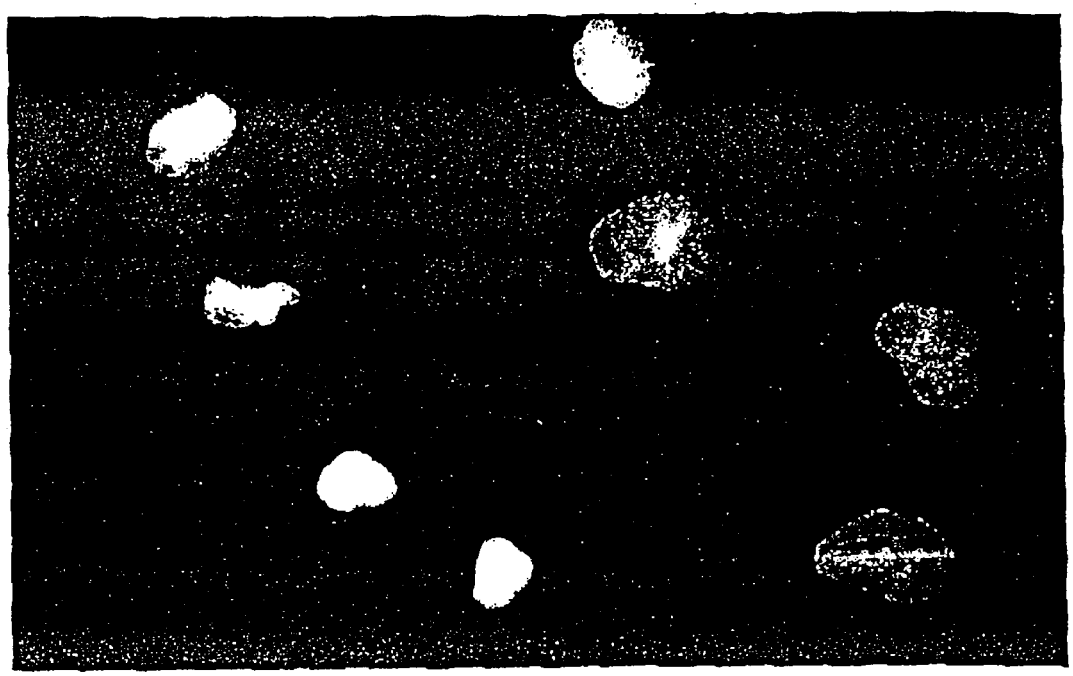
FIG. 6B shows endothelial cells upon staining with 4',6'-diamidino-2-phenylindole hydrochloride after four hours of exposure to $HK_a$.

Staining of cells with DAPI revealed nuclear condensation and fragmentation only in cells that had been exposed to $HK_a$; these changes were observed in 30–50% of the cells within 6 hours after $HK_a$ addition (FIG. 6A). Parallel studies in which cells were incubated with Trypan blue after incubation with $HK_a$ revealed no evidence of dye uptake, demonstrating that $HK_a$ did not induce cell lysis, and that its effects were due to the induction of apoptosis rather than cytotoxicity. Consistent with this observation, analysis of DNA isolated from cells incubated with $HK_a$ revealed striking fragmentation, which was first apparent approximately 6 hours after addition of the $HK_a$ (FIG. 7A). Consistent with these results, a specific "laddering" pattern of DNA fragmentation, characteristic of apoptosis, was apparent upon electrophoretic analysis of DNA from cells exposed to $HK_a$ (data not shown). Finally, flow cytometric analysis of cells incubated in the absence or presence of $HK_a$, and labeled with fluorescein dUTP by the TUNEL reaction, and revealed a rightward shift of the major peak only in cell populations exposed to $HK_a$ (not shown). As with DAPI staining and DNA fragmentation, these changes were apparent approximately 6 hours after exposure of cells to $HK_a$. Taken together, these studies demonstrate that the antiproliferative activity of $HK_a$ reflects its ability to induce endothelial cell apoptosis.

Example 3

Inhibition of Cytokine-Stimulated Angiogenesis by Two-Chain High Molecular Weight Kininogen In Vivo A. Experimental The effect of $HK_a$ on cytokine-stimulated angiogenesis in vivo was determined using a previously-described assay In which the neovascularization of a MATRIGEL® (Becton, Dickinson and Co.) "plug" containing bFGF Is assessed (Passaniti et al., Lab Invest 67:519–528, 1992). Briefly, athymic Ncr nude mice (78 weeks old, females) were injected subcutaneously on the left and right mid-back with 0.25 ml of chilled MATRIGEL® (Becton, Dickinson and Co.) containing 400 ng bFGF and 50 µg heparin, to which either 25 µl of PBS (left mid-back injection) or an equal volume of PBS containing 0.4 mg/ml $HK_a$ (right mid-back injection) had been added. Immediately after injection, the MATRIGEL® (Becton, Dickinson and Co. solidified and remained as a solid, subcutaneous plugs through the 4 day duration of the experiment At this point, mice were sacrificed, and the skin incised along the mid back and peeled back over the flanks to expose the MATRIGEL® (Becton, Dickinson and Co.) plugs. Plugs were then photographed prior to their excision, fixation and processing, as previously described (Passaniti et al., Lab Invest 67:519–528, 1992).

The effect of $HK_a$ on cytokine-stimulated angiogenesis in vivo was also determined using a rat corneal micropocket angiogenesis assay as previously described (Polverini et al., Meth. Enzymol. 198:440–450, 1991; Fournier et al., Inv. Opthal. Vis. Sci. 21:354, 1981). Pellets were prepared using 12% hydron. Control pellets contained bFGF (50 ng/pellet), while test pellets contained bFGF and $HK_a$ (final concentration 10 µM). A single pellet was implanted in a 2 mm pocket prepared in each cornea, 1 mm from the limbus. The left eye of each animal received the control pellet, while the right eye received the $HK_a$-containing pellet. Corneal neovascularization was measured after 7 days, at which time a digital image of each eye was obtained using a Nikon NS-1 slit lamp. To determine the total area of neovessels in each eye, digital images were analyzed using a Leica-Qwin (Northvale, N.J.) image analysis system (Conrad et al., Lab. Invest. 70:434, 1994).

B. Results

Figure 8A:
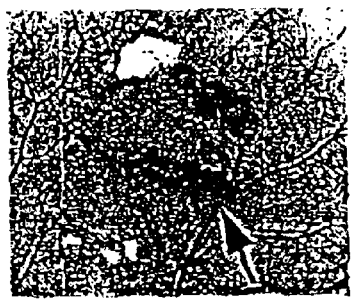
FIGS. 8A and 8B show athymic Ncr nude mice injected subcutaneously with chilled MATRIGEL® (Becton, Dickinson and Co.) containing bFGF which resulted in formation of a visible "plug". The plug was photographed four days post implantation.
Figure 8B:
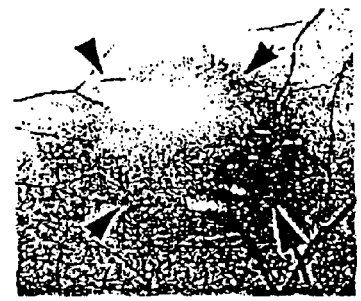
Figure 8C:
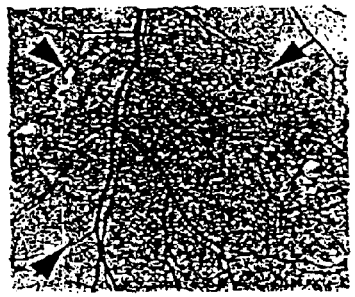
FIGS. 8C and 8D are similar to 8A and 8B except that the plug contained $HK_a$. The arrows in the figures point to the plug periphery. Plug vascularization is visible in FIGS. 8A and 8B, but absent in FIGS. 8C and 8D.
Figure 8D:

As depicted in FIGS. 8A and 8B, MATRIGEL® (Becton, Dickinson and Co.) plugs containing bFGF induced exuberant vessel ingrowth within 4 days after implantation. In contrast no neovascularization of MATRIGEL® (Becton, Dickinson and Co.) plugs which contained bFGF and $HK_a$ was observed (FIGS. 8C and 8D). In addition, these plugs remained transparent, as opposed to the opaque appearance acquired by the plugs, suggesting that $HK_a$ blocked the intravasation of migratory cells into the MATRIGEL® (Becton, Dickinson and Co.). The latter hypothesis was confirmed by histological analysis, which demonstrated markedly fewer cells within the $HK_a$-containing MATRIGEL® (Becton, Dickinson and Co.) plugs. Furthermore, the cells which had migrated Into these plugs appeared rounded and apoptotic, in contrast to the elongated, migratory phenotype of the cells invading the control plugs.

In the corneal micropocket angiogenesis assay, bFGF-containing hydron pellets implanted into control corneas induced a robust angiogenic response. In comparison, the length and density of neovessels were significantly reduced in corneas in which the implanted pellets contained bFGF and $HK_a$. Computer analysis of digital images revealed that the total vessel area within corneas that received $HK_a$-containing pellets (293,807 $\mu m^2$) was reduced by 82% in comparison to those in which pellets contained bFGF only (53,931 $\mu m^2$) (P<0.000000005).

Example 4

Effect of Peptide Analogs of Two-Chain High Molecular Weight Kininogen on Endothelial Cell Proliferation The following $HK_a$-derived peptides were synthesized:

Gly-His-Lys-Phe-Lys-Leu-Asp-Asp-Asp-Leu-Glu-His-Gln-Gly-Gly-His (SEQ ID NO:7);

Gly-His-Gly-His-Gly-His-Gly-Lys-His-Lys-Asn-Lys-Gly-Lys-Lys-Asn (SEQ ID NO:8); and His-Lys-Asn-Lys-Gly-Lys-Lys-Asn-Gly-Lys-His-Asn-Gly-Trp-Lys-Thr (SEQ ID NO:9).

The endothelial cell proliferation assay of Example 1 was performed, utilizing bFGF as the growth factor to stimulate angiogenesis and 50 µM of the above peptides. The same mathematical formula was employed but proliferation in the presence of GF plus peptide substituted for proliferation in the presence of GF plus $HK_a$. The percent inhibition of endothelial cell proliferation attributable to the peptides is given in Table 1. The value for $HK_a$ is also reported. The greater than 1 000/o inhibition level achieved in this assay with $HK_a$ (100% being no endothelial cell proliferation, that is, the level of proliferation in medium containing 2% serum alone, without added growth factor) reflects the fact that $HK_a$ induces endothelial cell apoptosis.

TABLE 1

Inhibition of Endothelial Cell Proliferation by $HK_a$ and $HK_a$-Derived Peptides

| Inhibitor (50 µM) | Inhibition of Endothelial Cell Proliferation | IC 50 |
|---|---|---|
| SEQ ID NO:7 | 59% | n.d. |
| SEQ ID NO:8 | 81% | 8 µM |
| SEQ ID NO:9 | 92% | 14 µM |
| $HK_a$ | 135% | 10 nM |

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A pharmaceutical composition comprising a pharmaceutically acceptable carrier and a compound of the formula $X_1$-His-Lys-X-Lys-$X_2$ wherein X is any amino acid, $X_1$ is the segment His-Gly-His-Glu-Gln-Gln-His-Gly-Leu-Gly-His-Gly (SEQ ID NO:1), or an N-terminal truncation fragment thereof containing at least one amino acid, and $X_2$ is (i) zero amino acids, or (ii) the segment Leu-Asp-Asp-Asp-Leu-Glu-His-Gln-Gly-Gly-His-Val (SEQ ID NO:2), or a C-terminal truncation fragment thereof containing at least one amino acid, and wherein said compound optionally comprises an amino-terminal protecting group and optionally comprises a carboxy-terminal protecting group.

2. The composition of claim 1 wherein $X_1$ is from one to six amino acids in length, and $X_2$ is from zero to six amino acids in length.

3. The composition of claim 1 wherein X is selected from the group consisting of Ala, Leu, Ile, Val, Pro, Phe, Trp, Met, Ser, Thr, Tyr, Asn, Gln, Cys, and Gly.

4. The composition of claim 3 wherein X is Asn, Phe or His.

5. The composition of claim 1 wherein the compound has the amino acid sequence His-Gly-His-Glu-Gln-Gln-His-Gly-Leu-Gly-His-Lys-Phe-Lys-Leu-Asp-Asp-Asp-Leu-Glu-His-Gln-Gly-Gly-His-Val (SEQ ID NO:5).

6. The composition of claim 1 wherein the compound has the amino acid sequence Gly-His-Lys-Phe-Lys-Leu-Asp-Asp-Asp-Leu-Glu-His-Gln-Gly-Gly-His(SEQ ID NO:7).

7. A method of inhibiting angiogenesis comprising administering to a mammal a pharmaceutical effective amount of a pharmaceutical composition comprising a pharmaceutically acceptable carrier and a compound of the formula $X_1$-His-Lys-X-Lys-$X_2$ wherein X is any amino acid, $X_1$ is from zero to twelve amino acids, and $X_2$ is from zero to twelve amino acids, and wherein said compound optionally comprises an amino-terminal protecting group and optionally comprises a carboxy-terminal protecting group.

8. A method of inhibiting angiogenesis comprising administering to a mammal a pharmaceutically effective amount of a single-chain high molecular weight kininogen.

9. A method of inhibiting angiogenesis comprising administering to a mammal a pharmaceutically effective amount of a single-chain high molecular weight kininogen.

10. A compound consisting of the formula $X_1$-His-Lys-X-Lys-$X_2$ wherein

X is any amino acid, $X_1$ is the segment His-Gly-His-Glu-Gln-Gln-His-Gly-Leu-Gly-His-Gly (Seq ID NO:1), or an N-terminal truncation fragment thereof containing at least one amino acid, and $X_2$ is
  (i) zero amino acids, or
  (ii) the segment Leu-Asp-Asp-Asp-Leu-Glu-His-Gln-Gly-Gly-His-Val (SEQ ID NO:2), or a C-terminal truncation fragment thereof containing at least one amino acid, and wherein said compound optionally comprises an amino-terminal protecting group and optionally comprises a carboxy-terminal protecting group.

11. The compound of claim 10 wherein X is Asn, Phe or His.

12. The compound of claim 10 having amino acid sequence His-Gly-His-Glu-Gln-Gln-His-Gly-Leu-Gly-His-Gly-His-Lys-Phe-Lys-Leu-Asp-Asp-Asp-Leu-Glu-His-Gln-Gly-Gly-His-Val (SEQ ID NO:5).

13. The compound of claim 10 having the amino acid sequence Gly-His-Lys-Phe-Lys-Leu-Asp-Asp-Asp-Leu-Glu-His-Gln-Gly-Gly-His (SEQ ID NO:7).

14. A compound consisting of the amino acid sequence Lys-His-Gly-His-Gly-His-Gly-Lys-His-Lys-Asn-Lys-Gly-Lys-Lys-Asn (SEQ ID NO:8).

15. A compound consisting of the amino acid sequence His-Lys-Asn-Lys-Gly-Lys-Lys-Asn-Gly-Lys-His-Asn-Gly-Trp-Lys-Thr (SEQ ID NO:9).

16. the method of claim 7, wherein $X_1$ is from zero to six amino acids, and $X_2$ is from zero to six amino acids.

17. The method of claim 7, wherein X is selected from the group consisting of Ala, Leu, Ile, Val, Pro, Phe, Trp, Met, Ser, Thr, Tyr, ASN, Gln, Cys and Gly.

18. The method of claim 17 wherein X is Asn, Phe, or His.

19. The method of claim 7, wherein $X_1$ is
  (i) zero amino acids, or
  (ii) the segment His-Gly-His-Glu-Gln-Gln-His-Gly-Leu-Gly-His-Gly (SEQ ID NO:1), or an N-terminal truncation fragment thereof containing at least one amino acid, and $X_2$ is
  (i) zero amino acids, or
  (ii) the segment Leu-Asp-Asp-Asp-Leu-Glu-His-Gln-Gly-Gly-His-Val (SEQ. ID NO:2), or a C-terminal truncation fragment thereof containing at least one amino acid.

20. The method of claim 19 wherein X is Asn, Phe or His.

21. The method of claim 7, wherein the compound has at least 30% amino acid sequence homology to the amino acid sequence His-Gly-His-Glu-Gln-Gln-His-Gly-Leu-Gly-His-Gly-His-Lys-Phe-Lys-Leu-Asp-Asp-Asp-Leu-Glu-His-Gln-Gly-Gly-His-Val (SEQ ID NO:5).

22. The method of claim 7, wherein the compound has the amino acid sequence His-Gly-His-Glu-Gln-Gln-His-Gly-Leu-Gly-His-Gly-His-Lys-Phe-Lys-Leu-Asp-Asp-Asp-Leu-Glu-His-Gln-Gly-Gly-His-Val (SEQ ID NO:5).

23. The method of claim 7, wherein the compound has the amino acid sequence Gly-His-Lys-Phe-Lys-Leu-Asp-Asp-Asp-Leu-Glu-His-Gln-Gly-Gly-His (SEQ ID NO:7).

24. The method of claim 7, wherein $X_1$ is
  (i) zero amino acids, or
  (ii) the segment Gly-His-Lys-His-Lys-His-Gly-His-Gly-His-Gly-Lys (SEQ ID NO:3) or an N-terminal truncation fragment thereof containing at least one amino acid, and $X_2$ is
  (i) zero amino acids, or
  (ii) the segment Gly-Lys-Lys-Asn-Gly-Lys-His-Asn-Gly-Trp-Lys-Thr (SEQ ID NO:4) or a C-terminal truncation fragment thereof containing at least one amino acid.

25. The method of claim 24 wherein X is Asn, Phe, or His.

26. The method of claim 24, wherein the compound has at least 30% amino acid sequence homology to the amino acid sequence Gly-His-Lys-His-Lys-His-Gly-His-Gly-His-Gly-Lys-His-Lys-Asn-Lys-Gly-Lys-Lys-Asn-Gly-His-Asn-Gly-Trp-Lys-Thr (SEQ ID NO:6).

27. The method of claim 24, wherein the compound has the amino acid sequence Gly-His-Lys-His-Lys-His-Gly-His-Gly-His-Gly-Lys-His-Lys-Asn-Lys-Gly-Lys-Lys-Asn-Gly-Lys-His-Asn-Gly-Trp-Lys-Thr (SEQ ID NO:6).

28. The method of claim 24, wherein the compound has the amino acid sequence Lys-His-Gly-His-Gly-His-Gly-Lys-His-Lys-Asn-Lys-Gly-Lys-Lys-Asn (SEQ ID NO:8).

29. The method of claim 24, wherein the compound has the amino acid sequence His-Lys-Asn-Lys-Gly-Lys-Lys-Asn-Gly-Lys-His-Asn-Gly-Trp-Lys-Thr (SEQ ID NO:9).

* * * * *

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Human high
      molecular weight kininogen (HK) domain 5 fragment

<400> SEQUENCE: 1

His Gly His Glu Gln Gln His Gly Leu Gly His Gly
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 2

Leu Asp Asp Asp Leu Glu His Gln Gly Gly His Val
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 3

Gly His Lys His Lys His Gly His Gly His Gly Lys
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 4

Gly Lys Lys Asn Gly Lys His Asn Gly Trp Lys Thr
 1               5                  10

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 5

His Gly His Glu Gln Gln His Gly Leu Gly His Gly His Lys Phe Lys
 1               5                  10                  15

Leu Asp Asp Asp Leu Glu His Gln Gly Gly His Val
            20                  25

<210> SEQ ID NO 6

```
<211> LENGTH: 28
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 6

Gly His Lys His Lys His Gly His Gly His Gly Lys His Lys Asn Lys
 1               5                  10                  15

Gly Lys Lys Asn Gly Lys His Asn Gly Trp Lys Thr
             20                  25

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 7

Gly His Lys Phe Lys Leu Asp Asp Leu Glu His Gln Gly Gly His
 1               5                  10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 8

Lys His Gly His Gly His Gly Lys His Lys Asn Lys Gly Lys Lys Asn
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Human HK
      domain 5 fragment

<400> SEQUENCE: 9

His Lys Asn Lys Gly Lys Lys Asn Gly Lys His Asn Gly Trp Lys Thr
 1               5                  10                  15
```